(12) United States Patent
Banov

(10) Patent No.: US 10,016,500 B2
(45) Date of Patent: *Jul. 10, 2018

(54) POLOXAMER-BASED PHARMACEUTICAL COMPOSITIONS FOR TREATING WOUNDS

(71) Applicant: Professional Compounding Centers of America (PCCA), Houston, TX (US)

(72) Inventor: Daniel Banov, Sugar Land, TX (US)

(73) Assignee: Professional Compounding Centers of America, Houston, TX (US)

( * ) Notice: Subject to any disclaimer, the term of this patent is extended or adjusted under 35 U.S.C. 154(b) by 80 days.

This patent is subject to a terminal disclaimer.

(21) Appl. No.: 14/640,002

(22) Filed: Mar. 5, 2015

(65) Prior Publication Data

US 2015/0250876 A1 Sep. 10, 2015

Related U.S. Application Data

(60) Provisional application No. 61/948,180, filed on Mar. 5, 2014.

(51) Int. Cl.
| | |
|---|---|
| *A61K 47/10* | (2017.01) |
| *A61K 31/496* | (2006.01) |
| *A61K 9/00* | (2006.01) |
| *A61K 9/16* | (2006.01) |

(52) U.S. Cl.
CPC .............. *A61K 47/10* (2013.01); *A61K 9/006* (2013.01); *A61K 9/1617* (2013.01); *A61K 31/496* (2013.01)

(58) Field of Classification Search
None
See application file for complete search history.

(56) References Cited

U.S. PATENT DOCUMENTS

2008/0160067 A1 * 7/2008 Boeckh ............... A61K 9/0019
424/441
2009/0214656 A1 * 8/2009 Berndl .................. A61K 9/146
424/489

OTHER PUBLICATIONS

In Pharma Technologist.com (http://www.in-pharmatechnologist.com/Processing/New-Lutrol-product-from-BASF?utm_source=copyright&utm_medium=OnSite&utm_campaign=copyright). Oct. 16, 2003.*

* cited by examiner

*Primary Examiner* — Celeste A Roney
(74) *Attorney, Agent, or Firm* — David G. Woodral; GableGotwals

(57) ABSTRACT

Compositions and methods for treating bacterial, fungal, and yeast infections in wounds are disclosed. The disclosed poloxamer-based pharmaceutical composition includes a micronized poloxamer composition base combined with one or more suitable active pharmaceutical ingredients (APIs), such as, antibacterial or antifungal, thereby resulting in a synergistic effect for the APIs. The micronized poloxamer composition within poloxamer-based pharmaceutical composition includes poloxamer 407 and poloxamer 188. Poloxamer-based pharmaceutical composition exhibits a particle size average of about 50 µm, which enhance APIs solubility. Additionally, poloxamer-based pharmaceutical composition can be delivered in a plurality of dosage forms, such as, powders, sprays, ointments, pastes, creams, lotions, solutions, and patches, among others.

8 Claims, 3 Drawing Sheets

300
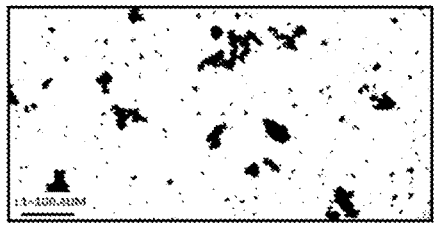
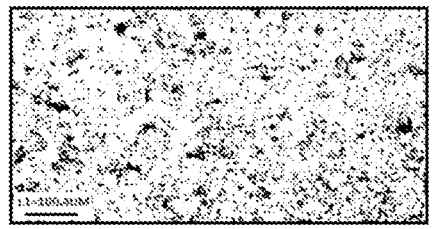
FIG. 3A  FIG. 3B
FIG. 3

POLOXAMER-BASED PHARMACEUTICAL COMPOSITIONS FOR TREATING WOUNDS

CROSS-REFERENCE TO RELATED APPLICATIONS

The present invention claims priority to U.S. Provisional Patent Application No. 61/948,180 filed Mar. 5, 2014, the entirety of which is incorporated herein by reference.

BACKGROUND

Field of the Disclosure

The present disclosure relates generally to pharmaceutical compositions, and more particularly, to poloxamer-based compositions for treating wounds.

Background Information

The development of a wound infection depends on the complex interplay of many factors. If the integrity and protective function of the skin is breached, large quantities of different micro-organisms can enter the wound and initiate an infection. The potential for infection depends on a number of patient variables, such as, the state of hydration, nutrition and existing medical conditions as well as extrinsic factors, for example, related to pre-, intra-, and post-operative care, if the patient has undergone surgery. The infections can be caused by infection agents, such as, viruses, viroids, prions, and micro-organisms, among others. The micro-organisms can be categorized into different groups, such as, bacteria, fungi, protozoa and viruses, depending on their structure and metabolic capabilities.

Fungal and yeast infections are the cause of a wide variety of diseases in mammals. While some fungi cause infections limited to the outermost layers of the skin and hair, other fungi may cause subcutaneous mycoses by penetrating into the keratinized layers of the skin, hair, and nails, and triggering pathologic changes in the host. Subcutaneous mycoses are often chronic, and cause infections in the dermis, subcutaneous tissue, muscle, and fascia.

Wounds usually allow microorganisms to gain access to tissues. Wound infections can occur as a result of penetrating trauma caused by plants, animals, or any type of objects. In an example, some plant parts (e.g., thorns) can puncture the skin and result in a wound infection. In another example, a thorn or other object can serve as a vector for the entry of *Staphylococcus aureus* or other organisms into the tissues. Furthermore, other types of trauma, such as, caused by animals and certain objects can result in long exposures to the surrounding environment, which can allow pathogen agents to penetrate through the layers of the skin and gain access to inner tissue.

Conventional treatment for fungal and yeast infections include topical and oral administration of drugs. Orally administered drugs are generally more effective than topically applied drugs. Oral administered drugs act systemically rather than locally and, therefore, the side effects of orally administered drugs can be much more severe. For example, human patients are at risk when taking strong antibiotics during long periods of time. This is because antibiotics kill both healthy and damaging bacteria. The killing of healthy bacteria can alter the balance of microorganisms in the mouth, vagina, intestines, as well as many other locations within the body. The reduction or elimination of microorganisms at certain location within the body can result in an overgrowth of fungus at those locations. Furthermore, individuals with weakened immune systems and/or diabetes are at risk of developing fungal infections more easily. Currently, topical antifungals are used for treating fungal and yeast infections located within human skin. However, the side effects for these compositions include skin rashes, itching, among others.

Accordingly, there is a need for new treatment options for patients affected by bacterial, fungal, or yeast infections; including treatment vehicles that allow more effective pharmaceutical compositions, and exhibit fewer side effects.

SUMMARY

The present disclosure relates to poloxamer-based pharmaceutical compositions. The poloxamer-based pharmaceutical compositions include micronized poloxamer compositions employed as a base having solubilizing properties combined with one or more active pharmaceutical ingredients (APIs). The micronized poloxamer compositions include a combination of two or more poloxamers. In some embodiments, the poloxamer-based pharmaceutical composition includes at least one antifungal agent and/or at least one antibiotic as API. In an example, the antifungal agent within the poloxamer based pharmaceutical composition is itraconazole.

In some embodiments, the poloxamer-based pharmaceutical composition is produced in the form of a sterile powder, which is combined with any suitable solvent, such as, water, ethanol, among others. In these embodiments, the micronized poloxamer composition within poloxamer-based pharmaceutical composition includes poloxamer 407 and poloxamer 188. Further to these embodiments, poloxamer 407 is included in amounts ranging from about 1% by weight to about 50% by weight, being preferably about 20% by weight. In these embodiments, poloxamer 188 is included in amounts ranging from about 1% by weight to about 50% by weight, being preferably about 20% by weight.

In other embodiments, the poloxamer-based pharmaceutical composition are produced in the form of a sterile powder and packaged in capsules. In these embodiments, the poloxamer-based pharmaceutical composition includes a stabilizing agent.

Numerous other aspects, features and benefits of the present disclosure may be made apparent from the following detailed description taken together with the drawing figures.

BRIEF DESCRIPTION OF THE DRAWINGS

The present disclosure can be better understood by referring to the following figures. The components in the figures are not necessarily to scale, emphasis instead being placed upon illustrating the principles of the disclosure. In the figures, reference numerals designate corresponding parts throughout the different views.

FIG. 3A is a graphical representation illustrating a particle size distribution of itraconazole when dispersed in purified water, according to an embodiment.

FIG. 3B is a graphical representation illustrating a particle size distribution of itraconazole in combination with micronized poloxamer composition when dispersed in purified water, according to an embodiment.

DETAILED DESCRIPTION

Figure 1:
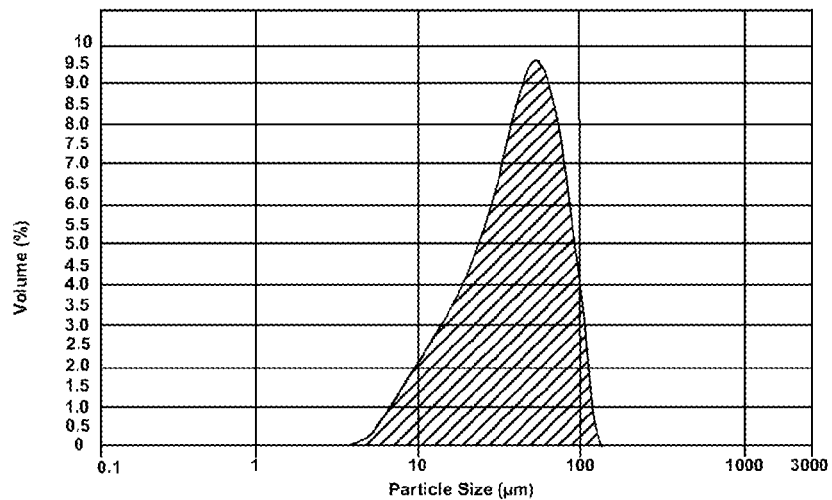
FIG. 1 is a graphical representation illustrating a particle size distribution curve of poloxamers, according to an embodiment.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the disclosure. One having ordinary skill in the relevant art, however, will readily recognize that the embodiments of the disclosure can be practiced without one or more of the specific details or with other methods. In other instances, well-known structures or operations are not shown in detail to avoid obscuring the aspects of the disclosure. The present disclosure is not limited by the illustrated ordering of acts or events, as some acts may occur in different orders and/or concurrently with other acts or events. Furthermore, not all illustrated acts or events are required to implement a methodology in accordance with the present disclosure.

Definitions

As used here, the following terms have the following definitions:

"Active Pharmaceutical Ingredients (APIs)" refer to chemical compounds that induce a desired effect, and include agents that are therapeutically or prophylactically effective.

"Microprilling" refers to a process where solid spherical microprills are produced from liquid, tablets, or encapsulated ingredients having a diameter of a few microns.

"Poloxamers" refers to non-toxic, non-ionic triblock copolymers composed of a central hydrophobic chain of polyoxypropylene (poly(propylene oxide)) flanked by two hydrophilic chains of polyoxyethylene (poly(ethylene oxide)).

"Vehicles" refers to carrier materials suitable for pharmaceutical or cosmetic formulations.

"Treating" and "treatment" refers to a wound cleaning process for reducing the severity and/or frequency of symptoms, elimination of symptoms and/or underlying cause, prevention of the occurrence of symptoms and/or their underlying cause, and improvement or remediation of damage in a wound or organ.

Description of the Disclosure

The present disclosure relates to poloxamer-based pharmaceutical compositions. The poloxamer-based pharmaceutical compositions include micronized poloxamer compositions employed as a base having solubilizing properties combined with one or more active pharmaceutical ingredients (APIs). The micronized poloxamer compositions include a combination of two or more poloxamers.

Micronized Poloxamer Composition

In some embodiments, a micronized poloxamer composition includes poloxamer 407 and poloxamer 188. In these embodiments, the poloxamer 407 is included in amounts ranging from about 1% by weight to about 50% by weight, being preferably about 20% by weight. Further to these embodiments, poloxamer 188 is included in amounts ranging from about 1% by weight to about 50% by weight, being preferably about 20% by weight.

In some embodiments, the manufacturing method of micronized poloxamer composition includes a non-contact mixing technology. In these embodiments, the non-contact mixing technology includes an apparatus for applying a low-frequency acoustic field to facilitate the mixing process. Further to these embodiments, the non-contact mixing creates micro-mixing zones throughout a mixing vessel, thereby providing a faster and more uniform mixing throughout the vessel.

In other embodiments, the particle size of poloxamer 407 and poloxamer 188 ranges from about 30 µm to about 70 µm, being preferably about 50 µm. In these embodiments, a microprilling process is used to produce microprills comprising poloxamer 407 and poloxamer 188. This poloxamer microprilling process produces a micronized poloxamer composition. Further to these embodiments, the advantages of the microprilling process when applied to poloxamer 407 and poloxamer 188 include: increased solubilization properties, controlled dissolution rate, reduction of die-wall friction, achievement of homogeneous blend, elimination of dose dumping, and effectiveness as water soluble lubricant, among others.

In some embodiments, the hydrophobic portion of the micronized poloxamer composition provides increased solubility properties. In these embodiments, when the micronized poloxamer composition is dissolved in any suitable solvent, such as water, the poloxamer molecules within the micronized poloxamer composition arrange themselves to form an "umbrella" like configuration. Further to these embodiments, the properties of each poloxamer are determined by the chain length of the polyxyethylene (EO-) units and polyoxypropyene (PO-) units, and vary in terms of molecular weight, appearance, hydrophilicity/hydrophobicity, and solubility.

Particle Size Distribution of Poloxamers

FIG. 1 is a graphical representation illustrating a particle size distribution curve of poloxamers, according to an embodiment. In FIG. 1, distribution curve 100 illustrates test results of particle size distribution of the microprilled poloxamers. In some embodiments, only the poloxamers exhibiting good blending homogeneity are used in direct compression to produce the microprilled poloxamers. In these embodiments, segregation problems associated with some poloxamer compositions are substantially reduced during the direct compression portion of the microprilling process when using the aforementioned poloxamers exhibiting good blending homogeneity.

In some embodiments, the microprilled poloxamer composition comprising poloxamer 407 and poloxamer 188 exhibits an average size of 50 µm. In these embodiments, a small percentage of the microprilled poloxamer composition comprising poloxamer 407 and poloxamer 188 exhibit a particle size ranging from about 10 µm to about 20 µm. Further to these embodiments, a considerable percentage of the microprilled poloxamer composition comprising poloxamer 407 and poloxamer 188 exhibits a particle size of about 50 µm.

Poloxamer-Based Pharmaceutical Composition Including Active Pharmaceutical Ingredients (APIs)

Figure 2:
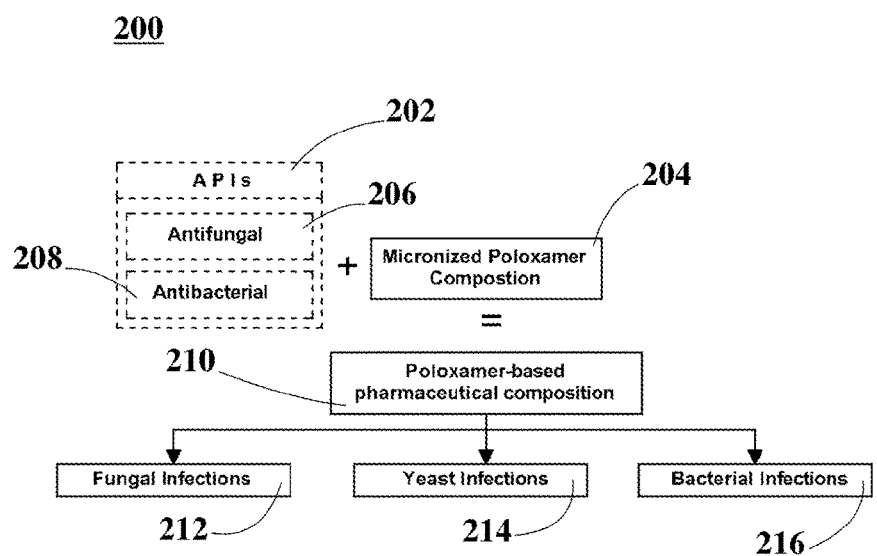
FIG. 2 is a graphical representation illustrating a block diagram for producing a poloxamer-based composition, according to an embodiment.

FIG. 2 is a graphical representation illustrating a block diagram for producing a poloxamer-based composition, according to an embodiment. In FIG. 2, block diagram 200 includes APIs 202, micronized poloxamer composition 204, antifungal agents 206, antibacterial agents 208, poloxamer-based pharmaceutical composition 210, fungal infections 212, yeast infections 214, and bacterial infections 216.

In some embodiments, micronized poloxamer composition 204 is combined with one or more APIs 202, such as, one or more antifungal agents 206 and/or one or more antibacterial agents 208. In these embodiments, before mixing micronized poloxamer composition 204 with one or more APIs 202, micronized poloxamer composition 204 is dissolved in a suitable solvent to produce poloxamer-based pharmaceutical composition 210. Further to these embodiments, poloxamer-based pharmaceutical composition 210 is employed for treating a plurality of infections, such as, fungal infections 212, yeast infections 214, or bacterial infections 216. In these embodiments, poloxamer-based pharmaceutical composition 210 exhibit effectiveness to treat wounds infected by fungi, bacterial, and yeast microorganisms.

In an example, poloxamer-based pharmaceutical composition 210 induces cell death in fungal microorganisms by inhibiting fungal cell wall synthesis, disrupting the cell membrane of the microorganism, affecting the ribosomal subunits to inhibit protein synthesis, altering protein synthesis, and the like.

In some embodiments, poloxamer-based pharmaceutical composition 210 is used for treating fungal infections 212 and yeast infections 214 in different organs, such as, nose, vagina, skin, and lungs, among others. In these embodiments, poloxamer-based pharmaceutical composition 210 can be administrated topically, orally, intranasal, or by inhalation. Further to these embodiments, poloxamer-based pharmaceutical composition 210 can treat infections caused by microorganisms, such as, *Escherichia coli, Staphylococcus aureus, Pseudomonas aeruginosa, Candida albicans, Aspergillus niger, Salmonella typhimurium*, methicillin resistant *Staphylococcus aureus, Aspergillus fumigatus*, and *Rhizopus oryzae*, among others. In an example, a suitable API within poloxamer-based pharmaceutical composition 210 is itraconazole. In this example, itraconazole has demonstrated to be consistent with the minimal inhibitory concentration (MIC) breakpoints values for all the aforementioned microorganisms. In these embodiments, poloxamer-based pharmaceutical composition 210, including itraconazole, approaches MIC values against filamentous fungi and yeast strains ranging from about 0.025 µg/mL to about 0.20 µg/mL.

Antifungal Agents

In some embodiments, antifungal agents include amrolfine, utenafine, naftifine, terbinafine, flucytosine, fluconazole, itraconazole, ketoconazole, posaconazole, ravuconazole, voriconazole, clotrimazole, econazole, miconazole, oxiconazole, sulconazole, terconazole, tioconazole, nikkomycin Z, caspofungin, micafungin, anidulafungin, amphotericin B, liposomal nystastin, pimaricin, griseofulvin, ciclopiroxolamine, haloprogin, tolnaftate, undecylenate, clioquinol, bifonazole, butoconazole, fenticonazole, isoconazole, omoconazole, sertaconazole, albaconazole, isavuconazole, abafungin, amorolfin, butenafine, and combinations thereof.

Antibiotic Agents

In other embodiments, antibiotic agents include aminoglycosides, amikacin, gentamicin, kanamycin, neomycin, netilmicin, tobramycin, paromomycin, spectinomycin, ansamycins, geldanamycin, herbimycin, rifaximin, carbacephem, loracarbef, carbapenems, ertapenem, doripenem, meropenem, cephalosporins, cefadroxil, cefazolin, cefalotin, cefalexin, cephalosporins, cefaclor, cefamandole, cefoxitin, cefprozil, cefuroxime, cephalosporins, cefixime, cefdinir, cefditoren, cefoperazone, cefotaxime, cefpodoxime, ceftazidime, ceftibuten, ceftizoxime, ceftriaxone, cephalosporins, cefepime, cephalosporins, ceftarolinefosamil, ceftobiprole, glycopeptides, teicoplanin, vancomycin, telavancin, lincosamides, clindamycin, lincomycin, lipopeptide, daptomycin, macrolides, azithromycin, clarithromycin, dirithromycin, erythromycin, roxithromycin, troleandomycin, telithromycin, spiramycin, monobactams, aztreonam, nitrofurans, furazolidone, nitrofurantoin, oxazolidonones, linezolid, posizolid, radezolid, torezolid, penicillins, amoxicillin, ampicillin, azlocillin, carbenicillin, cloxacillin, dicloxacillin, flucloxacillin, mezlocillin, methicillin, nafcillin, oxacillin, penicillin, piperacillin, temocillin, ticarcillin, polypeptides, bacitracin, colistin, polymyxin b, quinolones, ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin, sulfonamides, mafenide, sulfadiazine, sulfamethizole, sulfamethoxazole, sulfanilimide (archaic), sulfasalazine, sulfisoxazole, tetracyclines, demeclocycline, doxycycline, minocycline, oxytetracycline, tetracycline, clofazimine, dapsone, capreomycin, cycloserine, ethambutol, ethionamide, isoniazid, pyrazinamide, rifabutin, rifapentine, streptomycin, arsphenamine, chloramphenicol, fosfomycin, metronidazole, mupirocin, quinupristin/dalfopristin, thiamphenicol, tigecycline, trimethoprim, and combinations thereof.

Administration Route and Dosage form of Poloxamer-based Pharmaceutical Composition In some embodiments, poloxamer-based pharmaceutical composition 210 can be delivered in a plurality of dosage forms, such as, powders, sprays, ointments, pastes, creams, lotions, solutions, and patches, among others. In other embodiments, poloxamer-based pharmaceutical composition 210 is directly applied to any type of wound. In these embodiments, poloxamer-based pharmaceutical composition 210 is delivered by employing a spraying device.

In other embodiments, poloxamer-based pharmaceutical composition 210 is produced in the form of a sterile powder, which can be combined with any suitable solvent, such as water. In these embodiments, poloxamer-based pharmaceutical composition 210 in the form of sterile powder can be packaged in capsules and can include a stabilizing agent.

In some embodiments, poloxamer-based pharmaceutical composition 210 within a spraying device coats the exposed wound tissue before pathogens (e.g., bacteria, fungi, and/or yeast) break the continuous layers of the tissue. In these embodiments, poloxamer-based pharmaceutical composition 210 substantially inactivates or eliminates wound pathogens, thereby preventing the pathogen from inducing a pathogenic response. Further to these embodiments, the prevention and treatment of any wound infection also stimulates an immunological response against a specific pathogen, which can protect from further exposure to the same pathogen.

In other embodiments, poloxamer-based pharmaceutical composition 210 is applied to a wound with an effective dose from about 2 mL to about 15 mL, once or twice a day for a prescribed period of time. In these embodiments, poloxamer-based pharmaceutical composition 210 is produced taking advantage of the increased binding effect of some poloxamers and the associated gelling characteristics of their micronized poloxamer compositions. Further to these embodiments, poloxamer-based pharmaceutical composition 210 reach the affected site and remain at the infected site for longer periods of time to treat infections caused by micro-organisms, such as, *Escherichia coli, Staphylococcus aureus, Pseudomonas aeruginosa, Candida albicans, Aspergillus niger, Salmonella typhimurium*, methicillin resistant *Staphylococcus aureus, Aspergillus fumigatus*, and *Rhizopus oryzae*, among others.

Test #1. Antimicrobial Activity of Poloxamer-based Pharmaceutical Composition

Materials: Itraconazole EP Micronized (lot number C149307) and PCCA Formula #10342 (4 g of Itraconazole EP Micronized+37.574 g of Poloxamer composition) were provided by PCCA (Houston, Tex., USA) as powders. Itraconazole and PCCA Formula #10342 were prepared on the day of the assay. Fluconazole and amphotericin B were obtained as powders and stored at 4° C. Stock solutions (10.24 mg/mL) of these two reference actives were prepared in sterile water.

Strain: *Candida albicans* isolate ATCC 90028 was obtained from American Type Culture Collection (Manassas, Va.), and used in the course of this study.

Methods: In order to determine antimicrobial activity of itraconazole and the micronized poloxamer composition against biofilms of *Candida albicans*, an antifungal biofilm susceptibility testing was developed in conditions where a Minimum Biofilm Inhibitory Concentration (MBIC) of itraconazole within the micronized poloxamer composition, micronized poloxamer excipient, itraconazole, fluconazole and amphotericin B was measured for the *C. albicans* biofilm according to the conventional NCCLS M27-A broth microdilution method. The testing medium used for growing was RPMI 1640 (American Biorganics, Inc., Niagara Falls, N.Y.) supplemented with L-glutamine (Sigma Aldrich®). Yeast inocula (100 μL of 1×10$^6$ cells/mL) were added to each well of 96-well microtiter plates (Corning) and incubated at 37° C. for 48 h. After biofilm formation, medium was aspirated and non-adherent cells were sterile phosphate-buffered saline (PBS, Sigma Aldrich®). The antifungal drug and poloxamer mixture solutions (samples) were then added to the biofilms in serially diluted concentrations (1,024 to 0.5 μg/mL, from stock [concentrated] solutions of each sample prepared in RPMI medium directly) and incubated for a further 48 h at 35° C. A series of sample-free wells and biofilm-free wells were also included to serve as positive and negative controls, respectively. The MBIC was defined as the lowest concentration of sample that produced a 50% reduction of fungal growth compared with the growth control. Cell viability was determined by using a conventional CellTiter 96® Non-Radioactive Cell Proliferation Assay.

Results and Discussion: All biofilms formed on the microtiter plates over 48 h displayed consistent CellTiter 96® dye solution readings when the intensity of the colorimetric product was measured in a microtiter plate reader at 570 nm. The MBIC value of itraconazole within the micronized poloxamer composition (expressed as concentration of itraconazole) showed efficient result in comparison with the MBIC values for raw itraconazole, fluconazole and amphotericin B tested against *C. albicans* ATCC 90028, as detailed in Table 1. The micronized poloxamer composition improved the antimicrobial potential of itraconazole approximately 10-fold. Biofilm from *C. albicans* strain tested was intrinsically resistant to fluconazole (MBIC>1024 μg/mL). The polyene antifungal amphotericin B was highly active (MBIC=0.5 μg/mL) against *C. albicans* ATCC 90028. The findings for fluconazole and amphotericin B are in accordance with the current art.

In Table 1, itraconazole exhibits an increased in vitro antimicrobial activity against *candida* biofilms when associated with the micronized poloxamer composition. The in vitro antimicrobial activity is due to the benefits received from the use of the micronized poloxamer composition in terms of the dissolution rate and saturation solubility of the poorly water-soluble itraconazole, thus providing a higher in vitro dissolved drug concentration that induced an enhanced inhibition of microbial growth (considering the MIC). The micronized poloxamer composition including itraconazole exhibits improved particle size distribution in water, and also improved antifungal activity compared to itraconazole alone.

TABLE 1

Minimum Biofilm Inhibitory Concentrations against *C. albicans* ATCC 90028.

| Sample | Minimum Biofilm Inhibitory Concentration (ug/mL) |
|---|---|
| Amphotericin B | 0.5 |
| Fluconazole | >1,024 |
| Itraconazole | 1024 |
| Micronized Poloxamer Composition | >10,240 |
| Itraconazole/Micronized Poloxamer Composition | 98.5 |

Test #2 Particle Size Distribution of a Poloxamer-Based Pharmaceutical Composition The improvement of the dispersibility of APIs when used in combination with a micronized poloxamer composition was tested by a conventional optical microscopy methodology. For this study, itraconazole was chosen as the API due to its low solubility in water. FIG. 3A is a graphical representation illustrating a particle size distribution of itraconazole at 1% when dispersed in purified water, according to an embodiment. FIG. 3B is a graphical representation illustrating a particle size distribution of itraconazole at 1% in combination with micronized poloxamer composition when dispersed in purified water, according to an embodiment. Both at 200× magnification.

In FIG. 3B, the micronized poloxamer composition improves the particle size distribution of itraconazole within the solution, thus reducing particle size of itraconazole. Additionally, the synergistic effect of the micronized poloxamer composition is illustrated by the increased bioavailability and solubility of any suitable API, such as, itraconazole.

While various aspects and embodiments have been disclosed here, other aspects and embodiments may be contemplated. The various aspects and embodiments disclosed here are for purposes of illustration and are not intended to be limiting, with the true scope and spirit being indicated by the following claims.

What is claimed is:

1. A powdered pharmaceutical composition for wound treatment, consisting of a pharmaceutically effective amount of itraconazole particles, poloxamer 407 and poloxamer 188 wherein each of the poloxamer 407 and poloxamer 188 has a median particle size in the range of about 30 μm to about 70 μm.

2. The pharmaceutical composition of claim 1, wherein the poloxamer 407 is present in a range of about 1% to about 50% by weight.

3. The pharmaceutical composition of claim 1, wherein the poloxamer 407 is present at about 20% by weight.

4. The pharmaceutical composition of claim 1, wherein the poloxamer 188 is present in a range of about 1% to about 50% by weight.

5. The pharmaceutical composition of claim 1, wherein the poloxamer 188 is present at about 20% by weight.

6. The pharmaceutical composition of claim 1, wherein each of the poloxamer 407 and poloxamer 188 has a median particle size of about 50 μm.

7. The pharmaceutical composition of claim 1, wherein the itraconazole particles are mixed with the poloxamer 407 and poloxamer 188 by applying a low-frequency acoustic field.

8. The pharmaceutical composition of claim 1, wherein the poloxamer 407 and poloxamer 188 are produced using a microprilling process.

* * * * *